United States Patent [19]

Herold et al.

[11] Patent Number: 5,435,301
[45] Date of Patent: Jul. 25, 1995

[54] POWDER INHALER HAVING DISPERSING, DISCHARGE, AND DWELL-TIME CHAMBERS, ALONG WITH AN ACCELERATION CHANNEL

[75] Inventors: Heiko Herold, Neuss; Axel Wollenschläger, Leverkusen; Harald Landen; Franz Schmitt, both of Bergisch Gladbach, all of Germany

[73] Assignee: Bayer Aktiengesellschaft, Leverkusen, Germany

[21] Appl. No.: 153,708

[22] Filed: Nov. 17, 1993

[30] Foreign Application Priority Data

Nov. 24, 1992 [DE] Germany .................. 42 39 402.3

[51] Int. Cl.6 ................ A61M 15/00; A61M 16/10; B05D 7/14; B65D 83/06
[52] U.S. Cl. ....................... 128/203.15; 128/203.12
[58] Field of Search ............... 128/203.12, 203.15, 128/203.21; 604/58

[56] References Cited

U.S. PATENT DOCUMENTS

| | | | |
|---|---|---|---|
| 3,948,264 | 4/1976 | Wilke et al. | 128/203.15 |
| 4,064,878 | 12/1977 | Lundquist | 128/203.15 |
| 4,200,099 | 4/1980 | Guenzel et al. | 222/636 |
| 4,570,630 | 2/1986 | Elliott et al. | 128/203.15 |
| 4,668,218 | 5/1987 | Virtanen | 128/203.15 |
| 4,889,114 | 12/1989 | Kladders | 128/203.15 |
| 5,113,855 | 5/1992 | Newhouse | 128/203.15 |

FOREIGN PATENT DOCUMENTS

| | | | |
|---|---|---|---|
| 0069715 | 1/1983 | European Pat. Off. | 128/203.15 |
| 0237507 | 9/1987 | European Pat. Off. | 128/203.15 |
| 0407028 | 1/1991 | European Pat. Off. | 128/203.15 |
| 0488609 | 6/1992 | European Pat. Off. | 128/203.15 |
| 666823 | 8/1988 | Switzerland | 128/203.15 |
| 1122284 | 8/1968 | United Kingdom | 128/203.15 |
| 1331216 | 9/1973 | United Kingdom | 128/203.15 |
| 848035 | 7/1981 | U.S.S.R. | |
| 9007351 | 7/1990 | WIPO | 128/203.15 |
| 9102558 | 3/1991 | WIPO | 128/203.15 |
| 9112040 | 8/1991 | WIPO | 128/203.15 |
| 9209322 | 6/1992 | WIPO | 128/203.15 |
| 9218188 | 10/1992 | WIPO | 128/203.15 |

*Primary Examiner*—Kimberly L. Asher
*Attorney, Agent, or Firm*—Sprung Horn Kramer & Woods

[57] ABSTRACT

The powder inhaler is based on a supply container (3) for the drug, which supply container is partially or completely closed off at its lower end by a rotatable or displaceable, manually actuated metering plate (4) for the repeated reception and delivery of a predetermined, reproducible quantity of the drug from the container (3), and of a mouthpiece (14) for inhaling, upstream of which a dispersing chamber (12) is connected. The metering plate (4) is provided with at least one depression (5) which is filled with the drug on actuation of the inhaler. Seen in the flow direction, an acceleration channel is arranged ahead of the dispersing chamber (12), which acceleration channel (8) partially covers the metering plate (4) with part of its longitudinal surface and opens out tangentially into a cylindrical dwell-time chamber (9). The dwell-time chamber (9) is, in turn, connected via a central outlet (10) of smaller diameter than the cylindrical dwell-time chamber (9) to a circular discharge chamber (11) which the dispersing chamber (12) adjoins tangentially.

8 Claims, 2 Drawing Sheets

POWDER INHALER HAVING DISPERSING, DISCHARGE, AND DWELL-TIME CHAMBERS, ALONG WITH AN ACCELERATION CHANNEL

BACKGROUND OF THE INVENTION

The invention relates to a device for inhaling a powdery, micronized, pharmacologically active drug, which has been converted into a flowable formulation, having a supply container for the drug formulation, which supply container is completely or partially closed off at its lower end by a rotatable or displaceable, manually actuated metering plate for the repeated reception and delivery of a predetermined, reproducible quantity of the drug from the container. The drug formulation can consist of pure micronized active substance (e.g. soft pellets) or of a mixture with a pharmaceutically acceptable carrier (e.g. lactose monohydrate). Additionally, the device has a mouthpiece for inhaling, a dispersing chamber being connected upstream of said mouthpiece.

During inhalation, the metered drug is dispersed inside the inhaler into largely respirable particles of the active substance. It has been shown that numerous drugs can advantageously be administered into the lung as an aerosol. As a result, in many cases a particularly rapid effect of the drug is possible whilst maintaining a dose of the active substance which is very low and, at the same time, causes little stress to the patient.

Up to now, numerous apparatuses for administering an aerosol have been developed. For example, dissolved drugs can be nebulized so finely by means of compressed-air or ultrasonic nebulizers that the resultant aerosol is respirable. A disadvantage is the considerable energy requirement for these apparatuses for nebulizing the solutions into respirable droplets, which results in large apparatuses and means dependence on external energy sources (e.g. mains electricity, accumulators). Also, many drugs cannot be formulated as a stable aqueous solution.

Another way of administering active substances into the lung consists in dissolving or dispersing the active substance in a pressure-liquefied propellant. When this solution or dispersion is released by means of a metering system, the active substance is provided in a very fine form by the sudden evaporation of the propellant and can be inhaled.

These systems harbour a plurality of disadvantages, for example:

very many patients do not manage the required coordination between triggering of the puff discharge and the inhalation;

contribution to environmental pollution by propellant gases;

the patients are irritated by the cold shock due to evaporating propellant;

the high speed of the aerosol leads to appreciable quantities settling in the throat area and can favour side effects there;

in total, only small doses of active substance (about 1 to 2 mg) can be administered.

In order to overcome the disadvantages of the compressed-gas aerosols, a plurality of powder inhalers were developed, in which the inhalation air of the patient is used for dispersing the drug formulation. This dispenses with the coordination of breathing and triggering the dose which is difficult for the patient to manage.

An example of a commercially available powder inhaler is specified in the British Patents 1,122,284 and 1,331,216. This apparatus is loaded with hard gelatine capsules in which the active substance is situated in a micronized form. When the capsule has been opened by two needles, the capsule is set in rotation by the flow of respiratory air during inhalation, as a result of which the micronized active substance is dispersed into the air flow and passes via the inhalation air into the lungs of the patient.

The previously known powder inhalers still show disadvantages:

they have to be loaded and cleaned in a laborious manner;

generally several inhalations are required in order to empty the capsule completely;

patients can unintentionally breathe into the device, as a result of which moisture is precipitated therein, which has a very adverse effect on the metering precision and dispersion of subsequent doses of active substance;

some devices show a high resistance to breathing, which causes additional stress to the patients. Other devices require very high inspiratory flow rates in order to achieve satisfactory dispersion, which is achieved only to an insufficient extent, particularly by small children and older patients.

An example of a powder inhaler with multiple doses is described in EP 0,237,507 and in EP 0,069,715. In these cases, the active ingredient is moved from a reservoir via a perforated membrane into a flow channel and dispersed with the inhalation air of the patient. However, even this device has disadvantages:

dependence of the metering precision on the inhalation flow. In small inhalation flows, cases of incorrect metering and lack of metering were observed, which causes problems since the patient has no control over the delivery of the active substance due to the small quantities of active substance administered;

dependence of dispersion on the inhalation flow;

in this case, as also in the abovementioned single-dose devices, patients can unintentionally breathe into the device, as a result of which moisture is precipitated therein, which has a very adverse effect on the metering and dispersion of subsequent doses of active substance.

SUMMARY OF THE INVENTION

The object of the invention lies in developing a powder inhaler with multiple metering, which already leads to good dispersion of the formulation in the case of low inhalation flows and maintains a largely constant high dispersion level when the inhalation flow is increased. In this case and in the following text, a formulation is understood to be a mixture of active substance and inactive ingredient or a pure, e.g. agglomerated, active substance. A further object consists in avoiding negative influences on the metering precision and the hygiene of the device in the case of unintentional exhalation by unpractised patients (breathing out into the inhaler).

Setting out from the powder inhaler described at the beginning, this object is achieved according to the invention in that the metering plate has at least one depression to receive the drug and, seen in the flow direction, an acceleration channel is arranged ahead of the dispersing chamber, which acceleration channel partially covers the metering plate with part of its longitudinal surface and opens out tangentially into a cylindrical dwell-time chamber, and in that the dwell-time chamber is connected via a central outlet of smaller diameter than the cylindrical dwell-time chamber to a circular discharge chamber which the dispersing chamber adjoins tangentially.

A diffuser is preferably connected upstream of the mouthpiece to delay the aerosol emerging from the dispersing chamber.

According to a further development, the acceleration channel can be closed by an exhalation barrier in the form of an elastic valve flap which opens during inhalation and releases the aerosol flow.

This valve flap is preferably constructed as a volute spring which simultaneously covers and closes the acceleration channel and the depressions in the metering plate.

The supply container for the drug preferably has a kidney-shaped cross-section, the side walls being vertical or being constructed at a maximum inclination of 30° to the vertical plane.

The metering plate is expediently mounted in such a way that it partially closes off the lower region of the acceleration channel with part of its surface so that the depressions in this partial area lie directly below the acceleration channel, while the other depressions are located below the supply container.

According to a preferred embodiment, the depressions in the metering plate can have, in plan view, a rectangular, oval or circular contour, the greatest width of the depressions being smaller than or equal to the width of the supply container.

A further improvement consists in the fact that there is a desiccant in a separate receptacle in the container above the bulk of the drug.

The following advantages are achieved by the invention:

the device has a very high metering precision for flowable formulations (e.g. adhesive powder mixtures). Overdoses due to repeated turning of the metering wheel are not possible in this case. The active substance is dispersed into respirable particles to a very high proportion even at low flow rates. In suitable formulations, this high proportion also remains virtually constant at higher flow rates, i.e. the dose delivered is influenced only slightly by the inspiratory flow within a relatively wide range. An exhalation barrier prevents patients erroneously breathing into the device and thus contaminating it and possibly moistening the product. Furthermore, after every inhalation only an extremely small amount of the formulation remains in the device, which can easily be removed by cleaning which the patient can carry out. During inhalation the device has only a medium breathing resistance which patients do not consider to be unpleasant.

The invention is explained in greater detail below with reference to an exemplary embodiment illustrated in the drawings, in which:

DETAILED DESCRIPTION OF THE INVENTION

Figure 1:
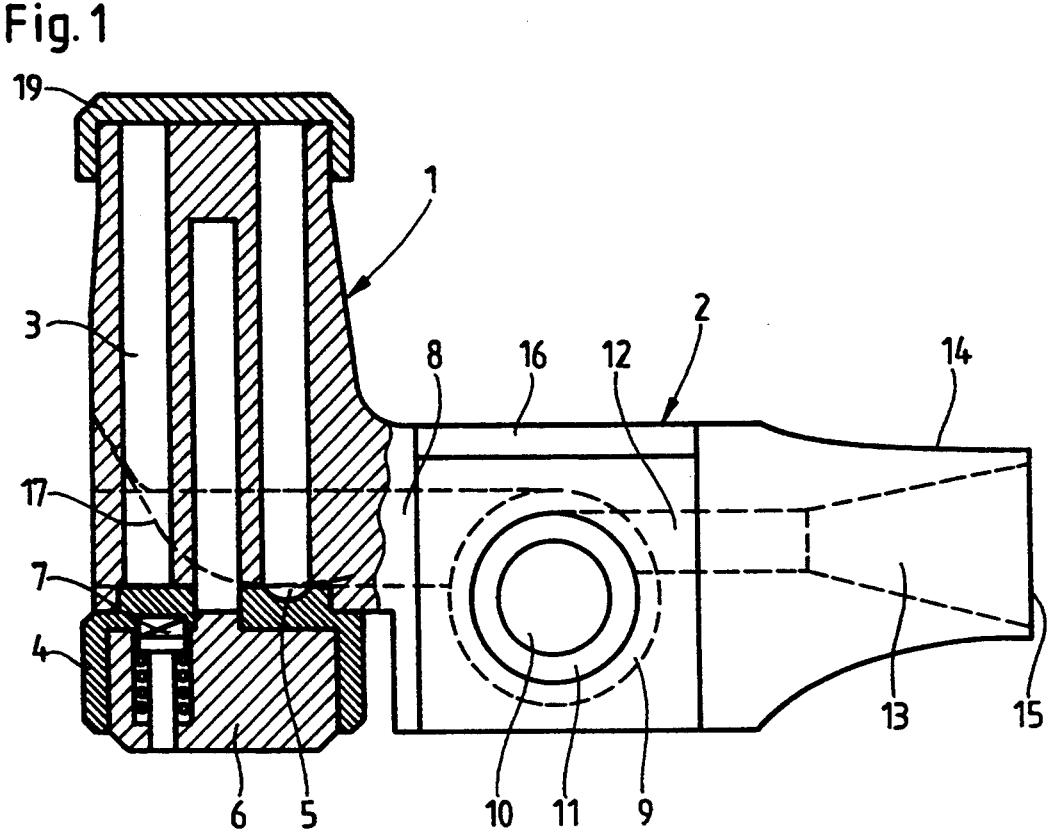
FIG. 1 shows a lateral view (with a partial section)

The powder inhaler according to FIG. 1 consists basically of a metering part 1 which is vertical in the position of use and an adjoining horizontal dispersing part 2. Accommodated in the metering part 1 is a semicircular or kidney-shaped supply container 3 for the flowable drug formulation. Arranged at the lower end of the metering part 1 is a metering wheel 4 which can be rotated about the longitudinal axis and has depressions 5. The depressions 5 are recessed into the horizontal surface of the metering wheel 4. The metering wheel 4 can rotate about a cylindrical bearing block 6 mounted at the lower end of the reservoir part. A latch 7 is provided inside the bearing block 6 to fix the metering wheel 4 in particular, predetermined angular positions. The outer surface of the metering wheel 4 is provided with a grooving in order to facilitate manual actuation.

Figure 2:
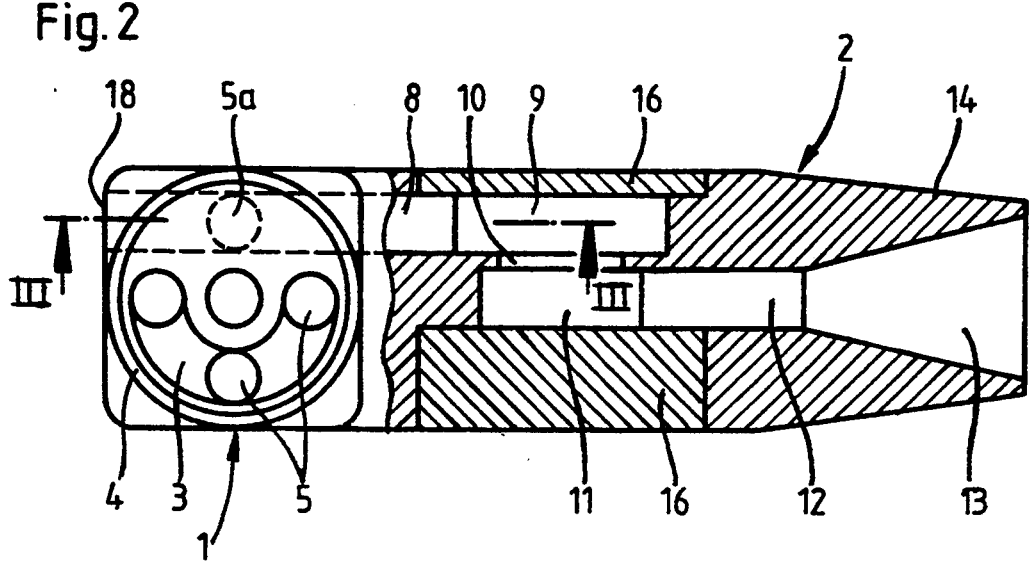
FIG. 2 shows a plan view (with a partial section)
Figure 3:
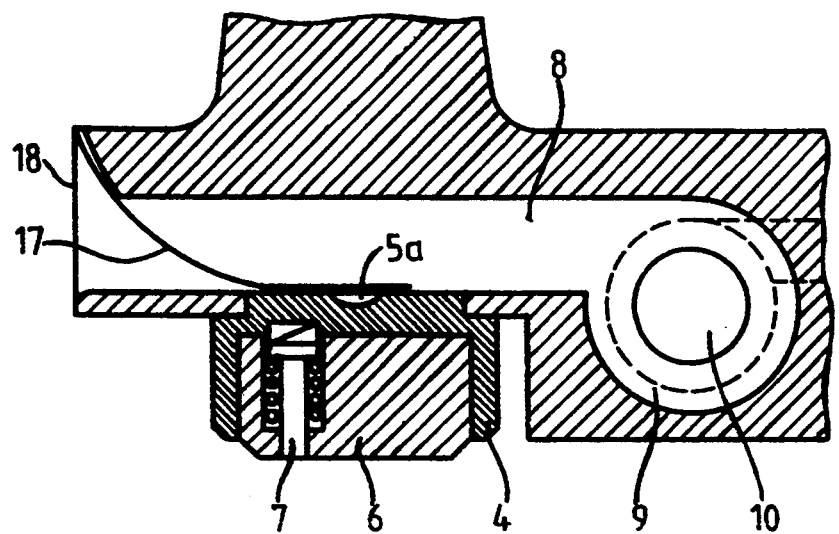
FIG. 3 shows an enlarged extract to illustrate the acceleration channel with the adjoining dwell-time chamber (section III—III in FIG. 2).

Above the metering wheel 4 (see also FIGS. 2 and 3), an acceleration channel 8 which is offset laterally relative to the mid-axis extends lengthwise through the dispersing part 2. It can be seen from FIG. 2 in conjunction with FIG. 1 that the acceleration channel 8 extends over part of the surface of the metering wheel. According to FIG. 2, the metering wheel 4 has four depressions 5, one of the depressions 5a lying just below the acceleration channel 8, while the other three depressions are located below the supply container 3. Instead of a plurality of depressions distributed evenly over the circumference, the metering wheel 4 can also have only a single depression 5. The acceleration channel 8 opens out tangentially into a cylindrical dwell-time chamber 9 which is connected via a central outlet 10 of smaller diameter than the cylindrical dwell-time chamber 9 to a circular discharge chamber 11. Adjoining the discharge chamber 11, likewise tangentially, is a dispersing chamber 12 which merges into a conically widened diffuser 13 located in the region of the mouthpiece. Due to the diffuser 13 in the mouthpiece 14, the aerosol flowing in from the dispersing chamber 12 is delayed in the direction towards the outlet aperture 15. The side walls of the dispersing part 2 are constructed in the form of a removable clip 16 so that the chambers 9, 11, 12, 13 are accessible for cleaning purposes (after removal of the clip 16).

FIG. 3 again shows the metering wheel 4 with the bearing block 6 and the laterally offset acceleration channel 8 arranged above the metering wheel. Arranged in the acceleration channel 8 is an exhalation barrier or valve flap in the form of a volute spring 17 which fills the entire cross-section of the acceleration channel 8 and lies diagonally in the channel 8 in the state of rest. The volute spring 17 can also be replaced by a spring-loaded, rigid metal sheet of a specifically predetermined shape. It is arranged in the acceleration channel in such a way that it not only closes the channel to the suction aperture 18 in the state of rest, but also, with its end, covers the depression 5a in the metering wheel 4 located in the region of the acceleration channel 8. It is thus achieved that a drug located in the depressions 5 cannot drop out even when the inhaler is turned. At the same time, the diagonally situated volute spring 17 prevents the possibility of exhalation through the device since the acceleration channel 8 is tightly blocked by the volute spring 17. In this manner, even in the case of coincidental and unintentional exhalations (breathing out), no moisture can pass into the depressions 5 and into the drug which is ready for metering. In contrast, during inhalation the volute spring 17 is raised by the negative pressure occurring during the inhalation process so that the acceleration channel 8, in dependence on the volume of the flow of inhaled air, and simultaneously also the depression 5a are exposed so that the flow passes over the depression 5a at high speed. Due to the turbulence of the flow, the powdery drug is discharged from the depression 5a into the acceleration channel 8.

The inhalation process and the mode of action of the powder inhaler are described below:

According to FIG. 1, the powdery, micronized, formulated drug to be inhaled is located in the supply container 3. Some of the depressions 5 in the metering wheel 4 (according to FIG. 2 all apart from the depression 5a) communicate with the container 3 and are filled up when the metering part 1 is in the vertical position. Before inhaling, the patient manually turns the metering wheel 4 on to the next engagement. In the process, a depression 5 filled with the powdery drug moves out of the region below the supply container 3 into the region of the acceleration channel, the metering wheel 4 with this depression 5a extending as a continuation of the lower longitudinal surface of the acceleration channel 8. In the embodiment having a single depression, the metering wheel would have to be turned on in this case through a larger angle until this depression is flush with the acceleration channel 8.

During inhalation, as described above, the volute spring 17 is raised and the drug is conveyed out of the depression 5a in the metering wheel 4 into the acceleration channel 8. From there, the powdery drug passes tangentially into the dwell-time chamber 9. Due to the delayed release from the dwell-time chamber 9, the formulation of active substance is subjected to the dispersing forces for a relatively long time so that, in total, improved dispersion into respirable particles of active substance is achieved. The particles already dispersed pass via the central outlet 10 into the discharge chamber 11.

Due to the dwell-time chamber 9, the delivery of active substance is thus delayed for a particular period. As a result, in contrast to powder inhalers according to the prior art, a large part of the drug is not already delivered at the beginning of the inhalation at a relatively low inhalation speed and thus in a poor state of dispersion.

From the discharge chamber 11, the drug is accelerated through the tangentially attached dispersing chamber 12 and is thus dispersed additionally. In the adjoining, conically widening diffuser 13 in the mouthpiece 14, the particle speed is delayed up to the outlet (outlet aperture 15), which reduces the probability of impact depositing of relatively small particles in the throat area.

The supply container 3 in the metering part 1 is closed by a reservoir lid 19. A small receptacle containing a desiccant can be accommodated in the lid 19 in order to protect the drug formulation in the supply container 3 from moisture.

We claim:

1. A device for inhaling a powdery, micronized and formulated, pharmacologically active drug in the form of an aerosol, comprising: a drug supply container having a lower end; a manually actuatable movable metering plate at least partially closing off the lower end of the supply container and repeatedly receptive of a drug in the supply container for delivering a predetermined reproducible quantity thereof and comprising at least one depression for receiving the drug; a mouthpiece for inhaling the drug by a user; a dispersing chamber upstream of the mouthpiece; a circular cross-section discharge chamber upstream of the dispersing chamber and to which the dispersing chamber is tangentially adjoined wherein a wall of the dispersing chamber merges into a circular wall of the discharge chamber forming a tangent thereto in cross-section, wherein the dispersing chamber, the discharge chamber, and their tangent connection all lie in a first plane; a cylindrical dwell time chamber upstream of the discharge chamber and having a central outlet having a smaller diameter than that of the dwell time chamber for connecting the dwell time chamber to the discharge chamber; and an elongated acceleration channel partially covering the metering plate and opening tangentially into the dwell time chamber wherein a wall of the acceleration channel merges into a cylindrical wall of the dwell time chamber forming a tangent thereto in cross-section, wherein the acceleration channel, the dwell time chamber, and their tangent connection all lie in a second plane, the central outlet connecting the first and second planes.

2. The device according to claim 1, wherein the inhaler has an outlet aperture and further comprising a diffuser between the dispersing chamber and the outlet aperture for delaying an aerosol emerging from the dispersing chamber.

3. The device according to claim 1, further comprising a valve flap in the acceleration channel mounted therein to open to allow aerosol flow during inhalation and close the channel to aerosol flow during exhalation.

4. The device according to claim 3, wherein the valve flap comprises a volute spring which simultaneously covers and closes the acceleration channel and the at least one depression in the metering plate.

5. The device according to claim 1, wherein the supply container has a kidney-shaped cross section with side walls having an inclination of from 0° to 30° to the vertical.

6. The device according to claim 1, wherein a partial area of the metering plate partially closes off a lower region of the acceleration channel.

7. The device according to claim 1, wherein the at least one depression has one of a rectangular, oval and circular contour wherein a greatest width is no greater than the width of the supply container.

8. The device according to claim 1, further comprising a lid for the supply container having a desiccant reservoir disposed above the drugs in the supply container.

* * * * *